(12) United States Patent
Erie et al.

(10) Patent No.: US 11,737,864 B2
(45) Date of Patent: Aug. 29, 2023

(54) INTRAOCULAR LENSES

(71) Applicant: Mayo Foundation for Medical Education and Research, Rochester, MN (US)

(72) Inventors: Jay C. Erie, Rochester, MN (US); Mark H. Bandhauer, Orange, CA (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 74 days.

(21) Appl. No.: 17/575,236

(22) Filed: Jan. 13, 2022

(65) Prior Publication Data

US 2022/0133468 A1  May 5, 2022

Related U.S. Application Data

(63) Continuation of application No. 16/769,787, filed as application No. PCT/US2018/067101 on Dec. 21, 2018, now Pat. No. 11,246,701.

(60) Provisional application No. 62/651,962, filed on Apr. 3, 2018, provisional application No. 62/609,637, filed on Dec. 22, 2017.

(51) Int. Cl.
*A61F 2/16* (2006.01)

(52) U.S. Cl.
CPC ............ *A61F 2/164* (2015.04); *A61F 2/1613* (2013.01); *A61F 2/1656* (2013.01); *A61F 2002/1681* (2013.01); *A61F 2002/1696* (2015.04); *A61F 2250/0053* (2013.01); *A61F 2250/0097* (2013.01)

(58) Field of Classification Search
CPC .................. A61F 2/1613; A61F 2/1656; A61F 2002/1696
See application file for complete search history.

(56) References Cited

U.S. PATENT DOCUMENTS

| | | |
|---|---|---|
| 4,634,442 A | 1/1987 | Link |
| 6,162,249 A | 12/2000 | Deacon et al. |
| 11,246,701 B2 | 2/2022 | Erie et al. |
| 2006/0142855 A1 | 6/2006 | Vaudant et al. |
| 2007/0276482 A1 | 11/2007 | Coroneo |
| 2008/0109077 A1 | 5/2008 | Bos |
| 2008/0269881 A1 | 10/2008 | Simpson et al. |
| 2008/0269882 A1 | 10/2008 | Simpson et al. |

(Continued)

FOREIGN PATENT DOCUMENTS

| | | |
|---|---|---|
| WO | WO 2015/033925 | 3/2015 |
| WO | WO 2016/058051 | 4/2016 |

OTHER PUBLICATIONS

Erie and Bandhauer, "Intraocular lens surfaces and their relationship to postoperative glare," Journal of Cataract & Refractive Surgery, 29(2):336-41, Feb. 2003.

(Continued)

*Primary Examiner* — Javier G Blanco
(74) *Attorney, Agent, or Firm* — Fish & Richardson P.C.

(57) ABSTRACT

This document describes intraocular lenses and methods for their use. For example, this document describes intraocular lenses that are shaped with a concave posterior peripheral portion that mitigates occurrences of dysphotopsia. The intraocular lenses described herein are designed to reduce positive and negative dysphotopsias after cataract surgery.

2 Claims, 11 Drawing Sheets

(56) References Cited

U.S. PATENT DOCUMENTS

| | | |
|---|---|---|
| 2008/0269884 A1 | 10/2008 | Vannoy |
| 2008/0269885 A1 | 10/2008 | Simpson et al. |
| 2008/0269886 A1 | 10/2008 | Simpson et al. |
| 2008/0269890 A1* | 10/2008 | Simpson ............... A61F 2/1613 623/6.46 |
| 2008/0269891 A1 | 10/2008 | Hong et al. |
| 2014/0005780 A1 | 1/2014 | Zhao |
| 2016/0095752 A1 | 4/2016 | Srinivasan et al. |
| 2017/0239040 A1 | 8/2017 | Coroneo |
| 2021/0169639 A1 | 6/2021 | Erie et al. |

OTHER PUBLICATIONS

Erie et al., "Analysis of postoperative glare and intraocular lens design," Journal of Cataract & Refractive Surgery, 27(4):614-21, Apr. 2001.
Holladay et al., "Negative dysphotopsia: the enigmatic penumbra," Journal of Cataract & Refractive Surgery, 38(7):1251-65, Jul. 2012.
International Preliminary Report on Patentability in International Application No. PCT/US2018/067101 dated Jun. 23, 2020, 7 pages.
International Search Report & Written Opinion in International Application No. PCT/US2018/067101 dated Mar. 8, 2019, 13 pages.
Masket et al., "Pseudophakic negative dysphotopsia: Surgical management and new theory of etiology," J. Cataract. Refract. Surgery, Jul. 2011, 37(7):1199-1207.
Vámosi et al., "Intraocular lens exchange in patients with negative dysphotopsia symptoms," J. Cataract. Refract. Surgery, Mar. 2010, 36(4):418-424.

* cited by examiner

—PRIOR ART—

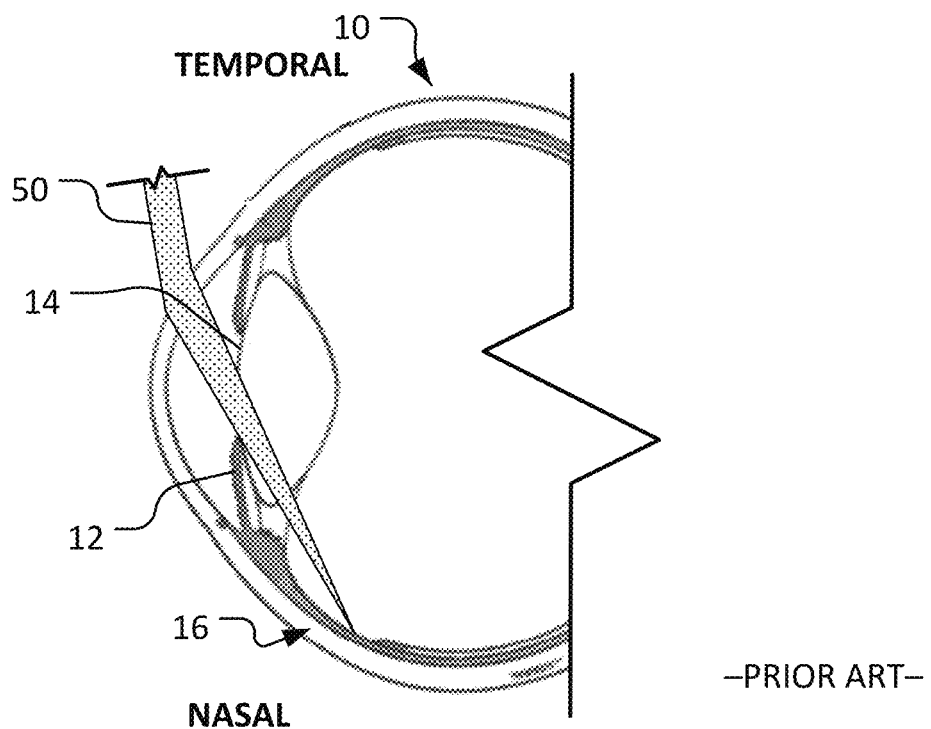
FIG. 2 —PRIOR ART—
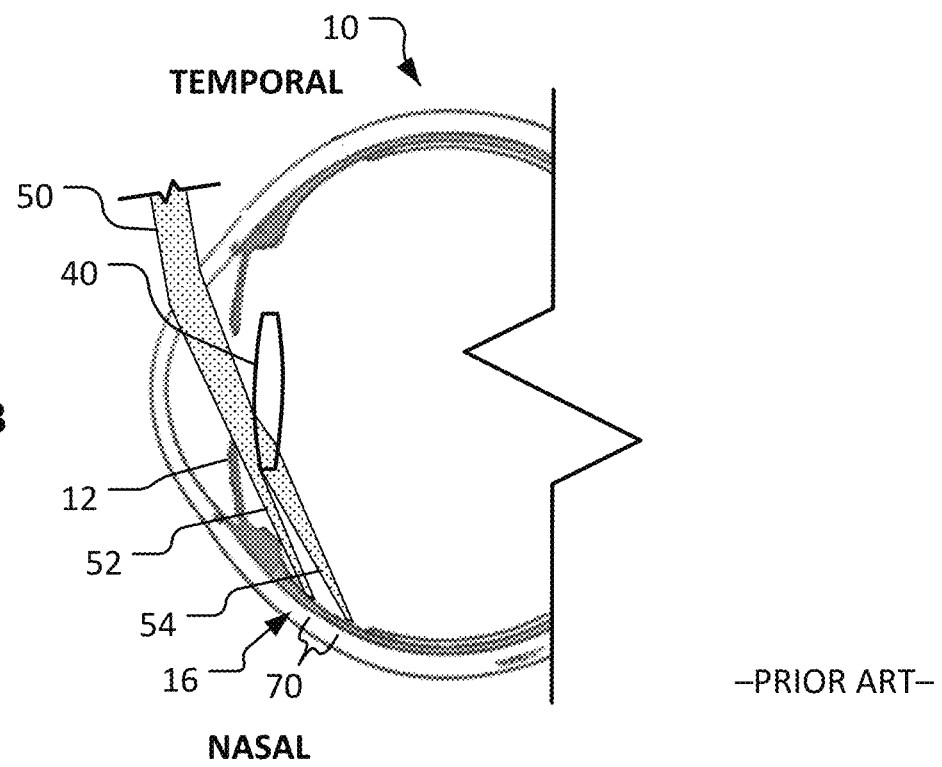
FIG. 3 —PRIOR ART—

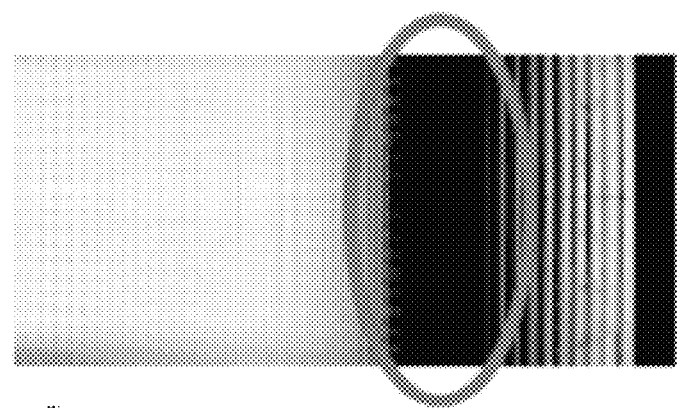
60°  FIG. 17  110°
Polar Plot
nasal                    temporal
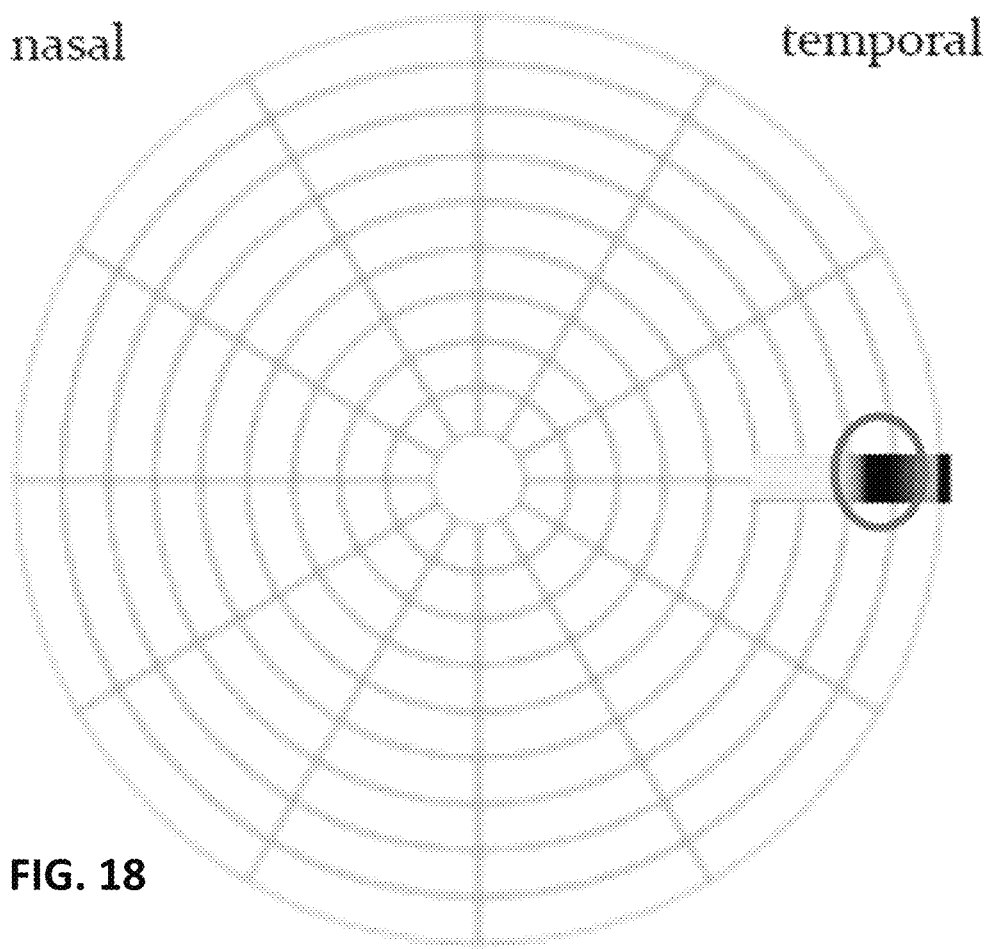
FIG. 18

INTRAOCULAR LENSES

CROSS-REFERENCE TO RELATED APPLICATIONS

This application is a continuation of U.S. application Ser. No. 16/769,787 filed Jun. 4, 2020, which is a National Stage Application under 35 U.S.C. § 371 that claims the benefit of Application Serial No. PCT/US2018/067101 filed Dec. 21, 2018, which also claims the benefit of U.S. Provisional Application Ser. No. 62/651,962 filed on Apr. 3, 2018, and U.S. Provisional Application Ser. No. 62/609,637 filed on Dec. 22, 2017. The disclosure of the prior applications are considered part of the disclosure of this application, and are incorporated in their entirety into this application.

BACKGROUND

1. Technical Field

This document relates to intraocular lenses and methods for their use. For example, this document relates to intraocular lenses (IOLs) that are shaped with a concave posterior peripheral portion to mitigate occurrences of dysphotopsia.

2. Background Information

There are about 2.5 million cataract surgeries in United States annually. Bothersome dark spots known as negative dysphotopsia (ND) occur in at least 15% of patients after cataract surgery, and persist in about 3% of patients at 1 year. In other words, approximately 75,000 persons in the U.S. are potentially affected by ND on an annual basis. Currently, there is no way to pre-operatively predict which patients are at risk for ND.

Investigators believe ND is due to light at the intraocular lens (IOL) periphery either refracted or missing the IOL, which distributes light unevenly—resulting in shadows on the retina, which are perceived as dark arcs by the patient.

SUMMARY

This document describes intraocular lenses and methods for their use. For example, this document describes intraocular lenses that are shaped with a concave posterior peripheral portion to mitigate occurrences of dysphotopsia.

In one aspect, this disclosure is directed to an intraocular lens that includes an anterior surface bounded by an edge, and a posterior surface bounded by the edge and opposing the anterior surface. The posterior surface includes a concave peripheral portion.

Such an intraocular lens may optionally include one or more of the following features. Portions of the posterior surface other than the concave peripheral portion may be convex. All other portions of the posterior surface other than the concave peripheral portion may be convex. An entirety of the anterior surface may be convex. The intraocular lens may also include two or more haptic members extending from the edge at respective haptic-optic junctions. One of the haptic members may extend from the edge at the concaved peripheral portion. The intraocular lens may also include at least one fiducial marker located on the intraocular lens.

In another aspect, this disclosure is directed to an intraocular lens that includes an anterior surface bounded by an edge and a posterior surface bounded by the edge and opposing the anterior surface. The posterior surface includes a concave portion.

Such an intraocular lens may optionally include one or more of the following features. The concave portion may extend along a portion of the posterior surface adjacent to a junction of the posterior surface and the edge. The edge may extend 360 degrees and the concave portion may extend along the portion of the posterior surface from between 80 degrees to 140 degrees. The concave portion may have a width between 0.25 mm to 0.75 mm. All other portions of the posterior surface other than the concave portion may be convex, and an entirety of the anterior surface may be convex. The intraocular lens may also include two or more haptic members extending from the edge at respective haptic-optic junctions. One of the haptic members may extend from the edge at the concaved portion. The intraocular lens may also include at least one fiducial marker located on the intraocular lens.

In another aspect, this disclosure is directed to a method of treating an eye that includes implanting an intraocular lens in the eye. The intraocular lens can include an anterior surface bounded by an edge, and a posterior surface bounded by the edge and opposing the anterior surface. The posterior surface includes a concave portion.

Such a method may optionally include one or more of the following features. The concave portion may be positioned at a nasal orientation relative to the eye. The intraocular lens may also include at least one fiducial marker located on the intraocular lens. The method may also include aligning the at least one fiducial marker at a nasal orientation relative to the eye.

Particular embodiments of the subject matter described in this document can be implemented to realize one or more of the following advantages. In some embodiments, instances of dysphotopsia after cataract surgery can be reduced using the intraocular lens designs described herein. Moreover, both negative and positive dysphotopsia can be potentially prevented or reduced. The intraocular lens designs described herein include posterior surface modifications that can be positioned along only a portion of the intraocular lens (e.g., about 90 to 120 degrees along the nasal aspect of the intraocular lens), rather than for 360 degrees around the entire intraocular lens periphery. As such, limiting the posterior surface treatment to a small portion of the intraocular lens optic may have some optical and manufacturing advantages. In some embodiments, the haptic portion of the intraocular lens is optically used to provide additional enhanced effects to reduce instances of dysphotopsia after cataract surgery.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 2 is a schematic illustration showing how light rays from the temporal field are received by a native crystalline lens and transferred to the nasal retina in the periphery. (The refractions at the surfaces of the lens are not shown in this diagram.)

FIG. 3 is a schematic illustration showing how light rays from the temporal field: (i) are received by a conventional prosthetic intraocular lens and are transferred to the nasal retina, and (ii) bypass the conventional prosthetic intraocular lens and extend to the nasal retina (The refractions at the lens are only shown in an approximate manner in this diagram.) The light rays from (i) and (ii) are spaced apart from each other on the nasal retina, resulting in the potential for dysphotopsia.

FIG. 17 is another depiction of the light intensity received at various locations on the peripheral retina while using a standard intraocular lens. Dark areas indicate shadow regions on the peripheral retina.

FIG. 18 shows the intensity display of FIG. 17 on a polar plot, simulating the visual field shadow in a temporal field seen by patients with negative dysphotopsia.

Like reference numbers represent corresponding parts throughout.

DETAILED DESCRIPTION

This document describes intraocular lenses and methods for their use. For example, this document describes intraocular lenses that are shaped with a concave posterior peripheral portion to mitigate occurrences of dysphotopsia. The intraocular lenses described herein are designed to reduce positive and negative dysphotopsias after cataract surgery.

Figure 1:
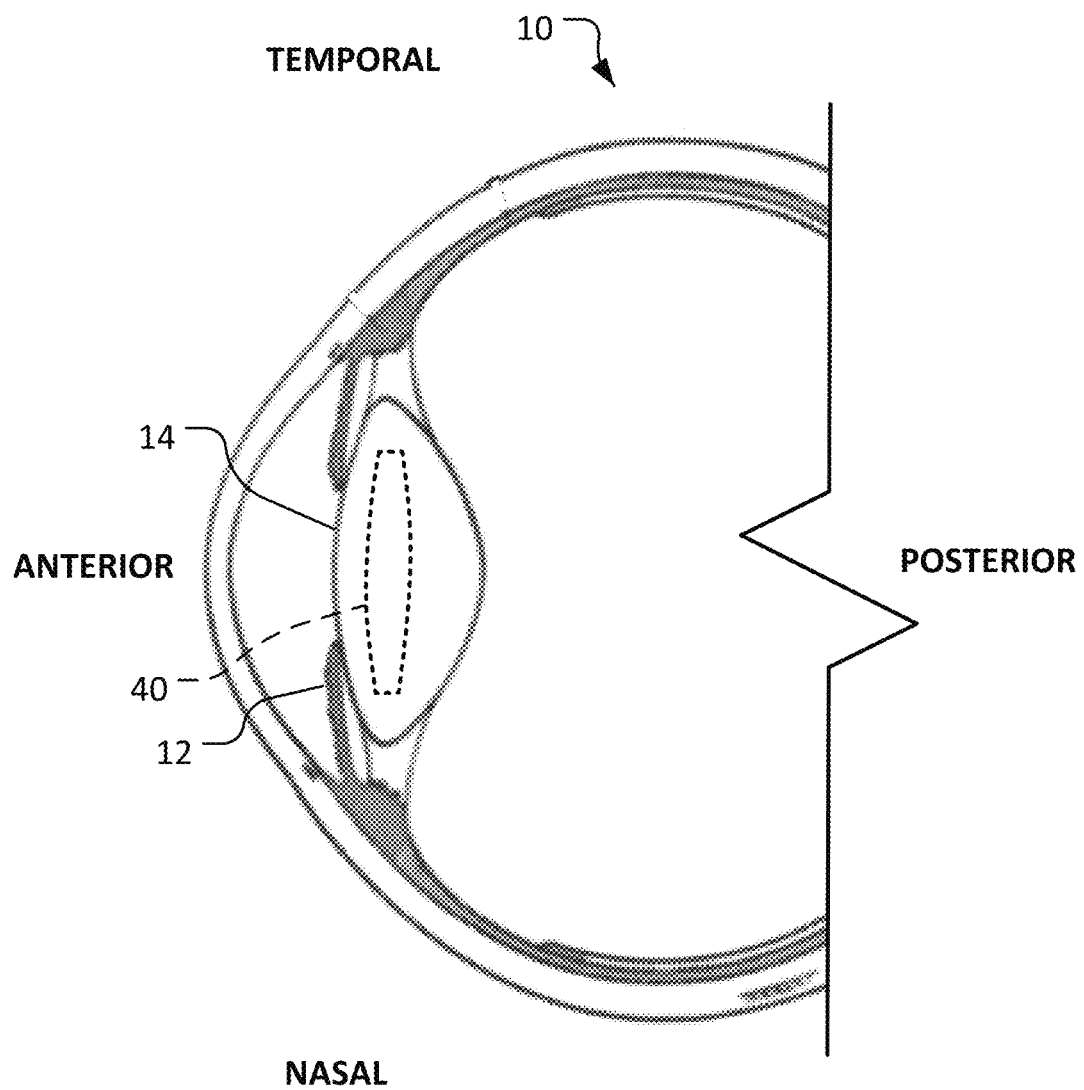
FIG. 1 is a schematic diagram of a transverse cross-section of an eye. A native crystalline lens is shown, and a conventional prosthetic intraocular lens is shown in broken lines (although the structures known as haptics, which hold the IOL optic body mechanically centered, are not shown).

FIG. 1 is a schematic diagram of a transverse cross-section of an eye 10 that includes an iris 12. Iris 12 is shown in its preoperative position. Eye 10 also includes a native crystalline lens 14.

A conventional prosthetic intraocular lens 40 is shown in broken lines. Intraocular lens 40 would be implanted after a cataract surgery to remove native crystalline lens 14. The relative size differences and location differences between native crystalline lens 14 and its replacement, prosthetic intraocular lens 40, are apparent in FIG. 1.

Prosthetic intraocular lens 40 is smaller than native crystalline lens 14. For example, in some cases the thickness of prosthetic intraocular lens 40 is about 20% of the thickness of the native crystalline lens 14. Also, the diameter of prosthetic intraocular lens 40 is smaller than the diameter of native crystalline lens 14. For example, in some cases the diameter of prosthetic intraocular lens 40 is between about 60-70% of the diameter of native crystalline lens 14.

It can also be seen that prosthetic intraocular lens 40 is implanted in a more posterior location than native crystalline lens 14. At least, the anterior surface of prosthetic intraocular lens 40 is in a more posterior location than the anterior surface of native crystalline lens 14. In result, iris 12 will deflect a little more posteriorly than shown in response to the removal of native crystalline lens 14. Even with such a deflection by iris 12, a space or gap will tend to exist between iris 12 and prosthetic intraocular lens 40.

Conventional prosthetic intraocular lens 40 has a convex anterior surface and a convex posterior surface. An entirety of the optical surfaces (anterior and posterior) of conventional prosthetic intraocular lens 40 are convex.

FIG. 2 is a schematic illustration showing how light rays 50 from the temporal field are received by native crystalline lens 14, and are transferred by native crystalline lens 14 to a nasal retina 16. One continuous group of light rays 50 are received by nasal retina 16. In other words, a single contiguous footprint is made by light rays 50 on nasal retina 16 after light rays 50 pass through native crystalline lens 14.

FIG. 3 is a schematic illustration showing how light rays 50 from the temporal field are received by standard/conventional prosthetic intraocular lens 40 and are transferred to nasal retina 16. A portion 52 of light rays 50 passes between iris 12 and conventional prosthetic intraocular lens 40. Light ray portion 52 thereby bypasses conventional prosthetic intraocular lens 40 and extends to nasal retina 16. Another portion 54 of light rays 50 passes through conventional prosthetic intraocular lens 40 and thereafter extends to nasal retina 16.

Light ray portion 52 and light ray portion 54 are spaced apart from each other on the nasal retina 16. In other words, the footprint made by light ray portion 52 on nasal retina 16 and the footprint made by light ray portion 54 on nasal retina 16 comprise two, separate spaced-apart footprints on nasal retina 16. Said differently, a gap 70 exists between the footprint made by light ray portion 52 on nasal retina 16 and the footprint made by light ray portion 54 on nasal retina 16. One of ordinary skill in the art will understand that the existence of gap 70 gives rise to the potential for dysphotopsia (e.g., negative dysphotopsia which can symptomatically include one or more arc-shaped shadows usually in the temporal field of vision, or positive dysphotopsia in the form of glare/halos/streaks).

Figure 16:
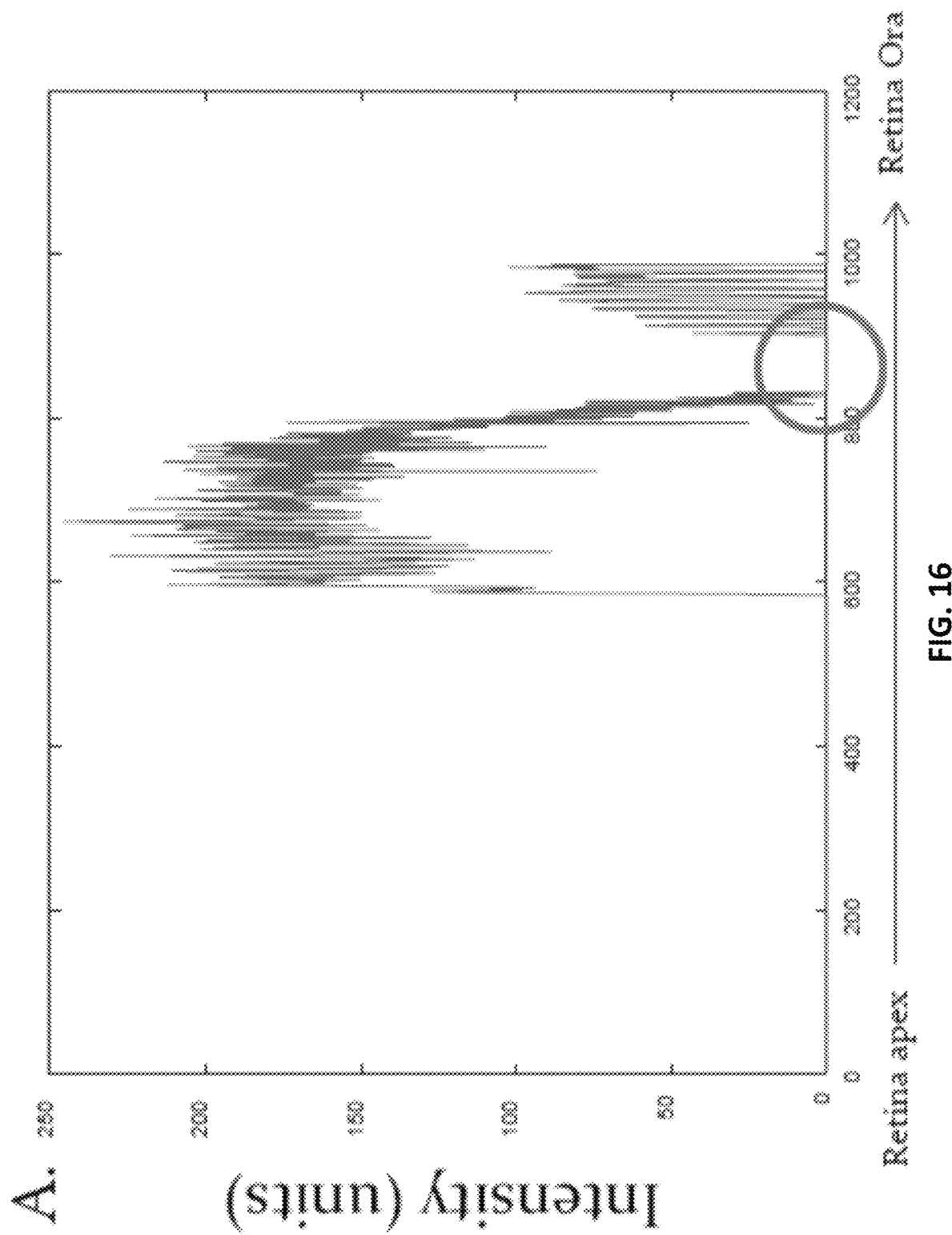
FIG. 16 shows a graph of light intensity received at various locations on the peripheral retina while using a standard intraocular lens.

FIG. 16 provides another representation of the phenomenon described in reference to FIG. 3. Here, a chart shows a graph of light intensity received at various locations on the peripheral retina while using a standard intraocular lens. The light intensity in the center region of the circled area is essentially zero, while being bounded on both sides by areas of greater light intensity. The circled location is consistent with the existence of one or more "shadow" region(s) that are symptomatic of negative dysphotopsia.

FIG. 17 shows another depiction of the retinal illumination in the peripheral retina while using a standard intraocular lens. The first dark area corresponds to a shadow region (e.g., at about 75-90 degrees).

FIG. 18 shows the intensity display of FIG. 17 on a polar plot, simulating the visual field shadow in a temporal field seen by patients with negative dysphotopsia.

Figure 4:
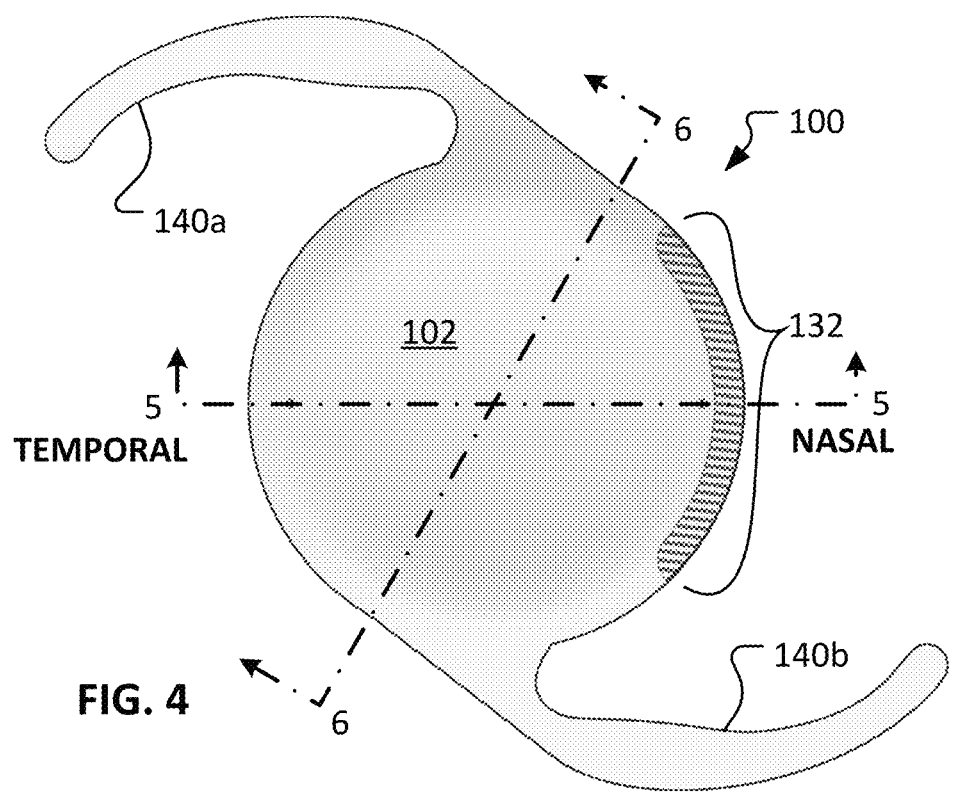
FIG. 4 shows a plan view of an example intraocular lens with a posterior surface that includes a localized concave peripheral portion in accordance with some embodiments described herein.
Figure 5:
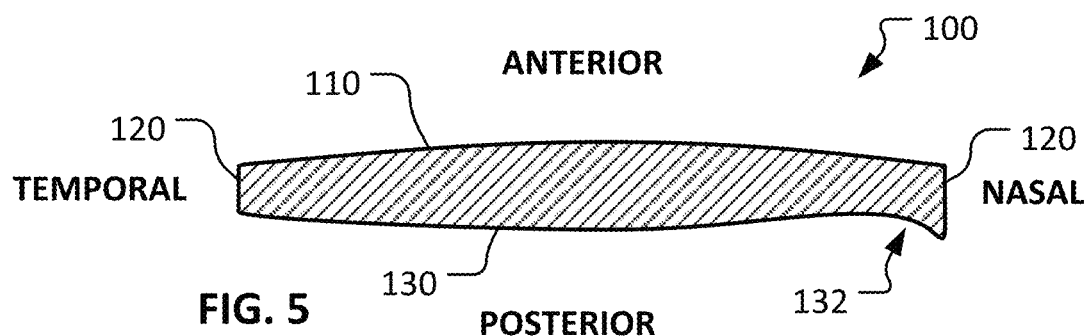
FIG. 5 shows a first cross-sectional view of the intraocular lens of FIG. 4.
Figure 6:
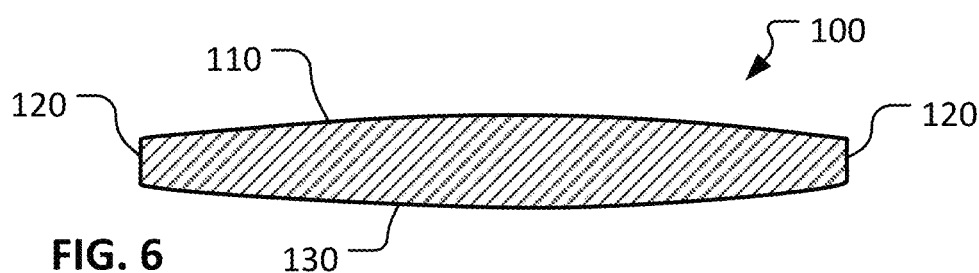
FIG. 6 shows a second cross-sectional view of the intraocular lens of FIG. 4.

An example intraocular lens 100 in accordance with some embodiments described herein is shown in FIGS. 4-6. FIG. 4 shows a plan view of intraocular lens 100. FIG. 5 shows a first cross-sectional view of intraocular lens 100, taken along section line 5-5. FIG. 6 shows a second cross-sectional view of intraocular lens 100, taken along section line 6-6.

Intraocular lens 100 includes a lens portion 102 and first and second haptic members 140a and 140b that extend from lens portion 102. Lens portion 102 includes an anterior surface 110, an edge 120, and a posterior surface 130. Anterior surface 110 and posterior surface 130 oppose each other.

In some embodiments, intraocular lens 100 is made of acrylic plastic that is molded, spun-cast, or made by cutting. Haptic members 140a and 140b can be integrally formed with lens portion 102, or separately formed and then attached to lens portion 102 (e.g., mounted in drilled holes).

Anterior surface 110 is convex. In some embodiments, anterior surface 110 is an aspheric convex surface. In some such embodiments, an entirety of anterior surface 110 can be an aspheric convex surface.

As depicted by FIG. 6, a majority of posterior surface 130 is convex. In some embodiments, that majority of posterior surface 130 is an aspheric convex surface. However, as depicted by FIGS. 4 and 5, posterior surface 130 includes a localized concave peripheral portion 132 (that may also be referred to as a "concave portion" or "concave periphery"). That is, while a majority of posterior surface 130 is convex, a discrete localized concave peripheral portion 132 extending near the edge 120 of posterior surface 130 is concave. As depicted in FIG. 4, the convex area of posterior surface 130 meets concave peripheral portion 132. In some embodiments, the convex area of posterior surface 130 and concave peripheral portion 132 meet by gradually blending into each other from a surface contour standpoint. In some embodiments, the convex area of posterior surface 130 and concave peripheral portion 132 meet with an abrupt transition (without blending).

In some cases, the width of concave peripheral portion 132 is about 1 millimeter (mm), or about 0.5 mm. In some cases, the width of concave peripheral portion 132 is in a range of about 0.25 mm to about 0.75 mm, or about 0.25 mm to about 0.50 mm, or about 0.20 mm to about 0.40 mm, or about 0.40 mm to about 0.60 mm, or about 0.30 mm to about 0.70 mm, or about 1 mm to about 2 mm, or about 0.8 mm to about 1.8 mm, or about 0.6 mm to about 1.6 mm, or about 0.8 mm to about 1.4 mm, or about 0.6 mm to about 1.2 mm, or about 0.8 mm to about 1.2 mm, or about 0.8 mm to about 1.0 mm, or about 0.6 mm to about 0.8 mm, without limitation. Such width ranges of the concave peripheral portion 132 are applicable to any of the lens designs described herein. Narrower widths (e.g., 0.5 mm and less) may advantageously tend to be less likely to contribute to visual artifacts and/or other disruptive optical effects.

In some cases, the concavity of concave peripheral portion 132 has a radius of curvature in a range of about 10 mm to about 50 mm, or about 30 mm to about 50 mm, or about 20 mm to about 60 mm, or about 10 mm to about 40 mm, or about 10 mm to about 30 mm, or about 40 mm to about 80 mm, without limitation. Such radius ranges of the concave peripheral portion 132 are applicable to any of the lens designs described herein.

Concave peripheral portion 132 extends along just a portion of edge 120. In some cases, concave peripheral portion 132 extends for about 120 degrees of the 360 degrees of edge 120. In some cases, concave peripheral portion 132 extends for about 90 degrees of the 360 degrees of edge 120. In some cases, concave peripheral portion 132 extends in a range of about 100 degrees to about 140 degrees, or about 80 degrees to about 160 degrees, or about 80 degrees to about 140 degrees, or about 60 degrees to about 120 degrees, or about 110 degrees to about 130 degrees, or about 80 degrees to about 100 degrees, or about 60 degrees to about 180 degrees. In some cases, concave peripheral portion 132 extends for all 360 degrees of the 360 degrees of edge 120. Such ranges of radial extension of the concave peripheral portion 132 are applicable to any of the lens designs described herein. Concave peripheral portions that are arcuate segments (e.g., extending less than 360 degrees) may be advantageous to preserve aspheric treatments to lens periphery to help users see with better contrast sensitivity. Embodiments with two segments (180 degrees from each other) would allow the surgeon to orient either of the modified portions nasally. Even with two modified segments, about one half of the optic edge periphery would be maintained as originally designed, to lessen the chance of affecting foveal vision or inducing unwanted artifacts.

Limiting the concave peripheral portion 132 to a portion of the 360 degrees of edge 120 may facilitate some optical and manufacturing advantages. By limiting the concave peripheral portion 132 to a portion of the 360 degrees of edge 120, any other portion of the IOL that does not contribute to ND reduction can be maintained as the convex posterior surface for the best imaging with regular foveal vision. The extent of the concavity of concave peripheral portion 132 is selectable.

The depth of concave peripheral portion 132 is exaggerated in FIG. 5 so that the general shape of concave peripheral portion 132 can be clearly envisioned. The intersection of concave peripheral portion 132 and edge 120 is a sharp edge (and more sharp and pointed than the intersection of posterior surface 130 and edge 120 at regions other than concave peripheral portion 132). The edge 120 may be frosted or not frosted.

In the depicted embodiment, edge 120 is parallel to the central axis of intraocular lens 100 (the central axis being orthogonal to the paper in the context of FIG. 4, and being within the plane of the paper in the context of FIGS. 5 and 6). Accordingly, edge 120 is essentially cylindrical (not frustoconical).

As described further below, concave peripheral portion 132 alters the peripheral optic surface curvature of intraocular lens 100 to maintain all available light on the light-sensitive retina but redirects it in such a way that it falls more uniformly on the retina, avoiding creating bright areas (positive dysphotopsia) and shadows (negative dysphotopsia).

Figure 7:
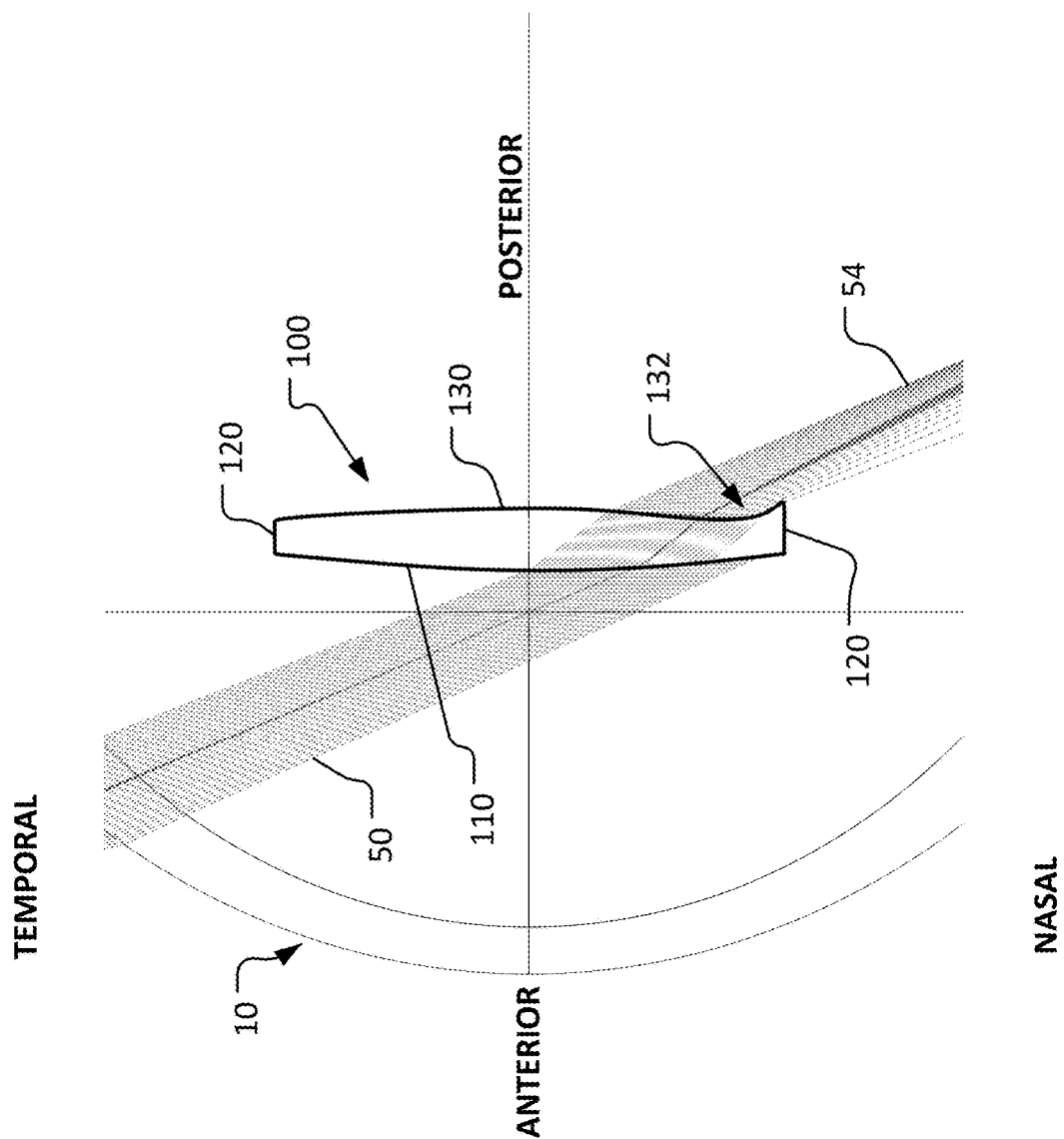
FIG. 7 is a schematic illustration showing how light rays from the temporal field are received and transmitted by an example intraocular lens in accordance with some embodiments described herein.

FIG. 7 is a schematic illustration showing how light rays 50 from the temporal field are received and transmitted by example intraocular lens 100. It is noteworthy that the shape of concave peripheral portion 132 causes part of light ray portion 54 to be fanned outward to a greater extent as compared to a convex-shaped posterior surface (e.g., as with a conventional intraocular lens such as the conventional intraocular lens 40 shown in FIG. 3). Consequently, the footprint on nasal retina 16 of light ray portion 54 is enlarged, thereby reducing or eliminating gap 70 (shown in FIG. 3).

Ray trace analysis shows that rays entering a pseudophakic eye from light sources between 70-90 degrees of visual angle can be refracted to different positions on the peripheral retina through specific intraocular lens design modifications such as having a concave peripheral posterior surface portion. The new positioning of the theoretical ray paths provides more uniform illumination of the peripheral retina. Analysis indicates that specific intraocular lens optic design modifications that alter how light entering the eye at large visual angles is diverged and redirected onto the peripheral retina may result in reduced rates of dysphotopsia after cataract surgery.

The modified intraocular lens design (to include the peripheral posterior concave portion) can be made less dependent on the IOL diopter power if the Anterior Chamber Depth, A-constant, or other Lens Constants are taken into account during the design process. Also, Astigmatism-correcting Toric IOLs can be made to include the peripheral posterior concave portion as described herein. In some cases, a right eye and a left eye specific design is used. Alternatively, in some cases a universal design is used (not right eye and left eye specific).

Figure 8:
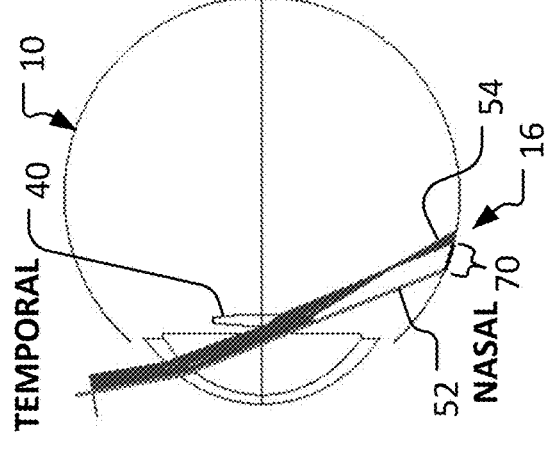
FIGS. 8 and 9 are schematic illustrations showing how light rays at 70 degrees and 80 degrees from the temporal field are received by a conventional prosthetic intraocular lens and are transmitted to the nasal retina, and how some of the light rays bypass the conventional prosthetic intraocular lens and extend to the nasal retina, resulting in a gap space on the nasal retina. The rays bypassing the IOL are incident at 70 degrees in both figures, and in the next figures (FIGS. 10 and 11).
Figure 9:
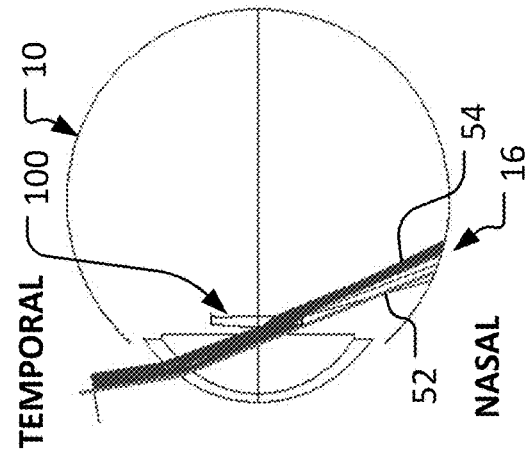

FIGS. 8 and 9 are schematic illustrations showing how light rays from the temporal field at 70 degrees and 80 degrees, respectively, are received by conventional prosthetic intraocular lens 40 and are transmitted to the nasal retina 16 as light ray portion 54. It can also be seen how some of the light rays from the temporal field at 70 degrees and 80 degrees bypass intraocular lens 40 and extend to the nasal retina 16 as light ray portion 52. (The rays bypassing the IOL are incident at 70 degrees in both figures, and in the next two similar figures.) Gap space 70 on nasal retina 16 between the footprints of light ray portions 52 and 54 is created. Accordingly, shadows (negative dysphotopsia) corresponding to gap space 70, and bright areas (positive dysphotopsia), may result with the use conventional prosthetic intraocular lens 40.

Figure 10:
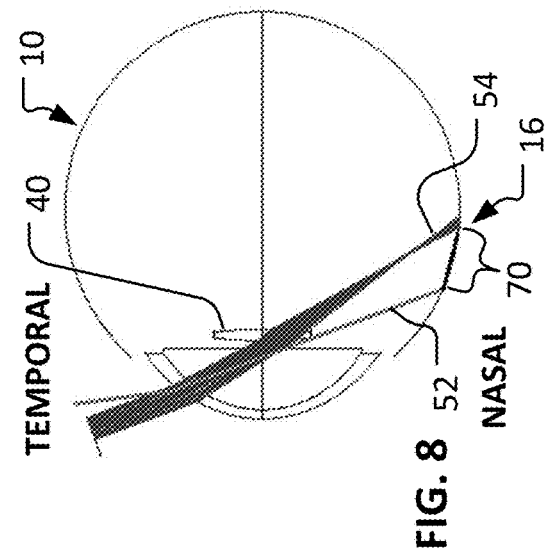
FIGS. 10 and 11 are schematic illustrations showing how light rays at 70 degrees and 80 degrees from the temporal field are received and transmitted by an example intraocular lens in accordance with some embodiments described herein. Such light rays transmitted to the nasal retina are spread more uniformly than the conventional lens of FIGS. 8 and 9. Consequently, the gap on the nasal retina between the footprints of the light rays transmitted by the intraocular lens and the light rays bypassing the intraocular lens is lessened as compared to the conventional lens of FIGS. 8 and 9.
Figure 11:
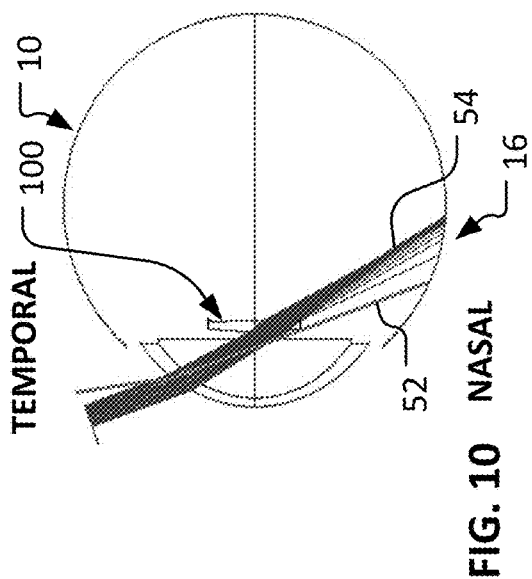

FIGS. 10 and 11 are schematic illustrations showing how light rays from the temporal field at 70 degrees and 80 degrees, respectively, are received and transmitted to the nasal retina 16 by intraocular lens 100 having a concave posterior peripheral portion 132 (e.g., refer to FIGS. 4-7). It can be seen how some of the light rays from the temporal field at 80 degrees bypass intraocular lens 100 and extend to the nasal retina as light ray portion 52. However, light ray portion 54 (which passes through intraocular lens 100) is shaped by concave posterior peripheral portion 32 such that at least a part of the light ray portion 54 is transmitted to nasal retina 16 while being spread to create a broader footprint on nasal retina 16 in comparison to conventional intraocular lens 40 (FIGS. 8 and 9). Consequently, the gap space on nasal retina 16 between the footprints of the light rays 52 and 54 transmitted by intraocular lens 100 is reduced as compared to conventional lens 40 of FIGS. 8 and 9.

Figure 19:
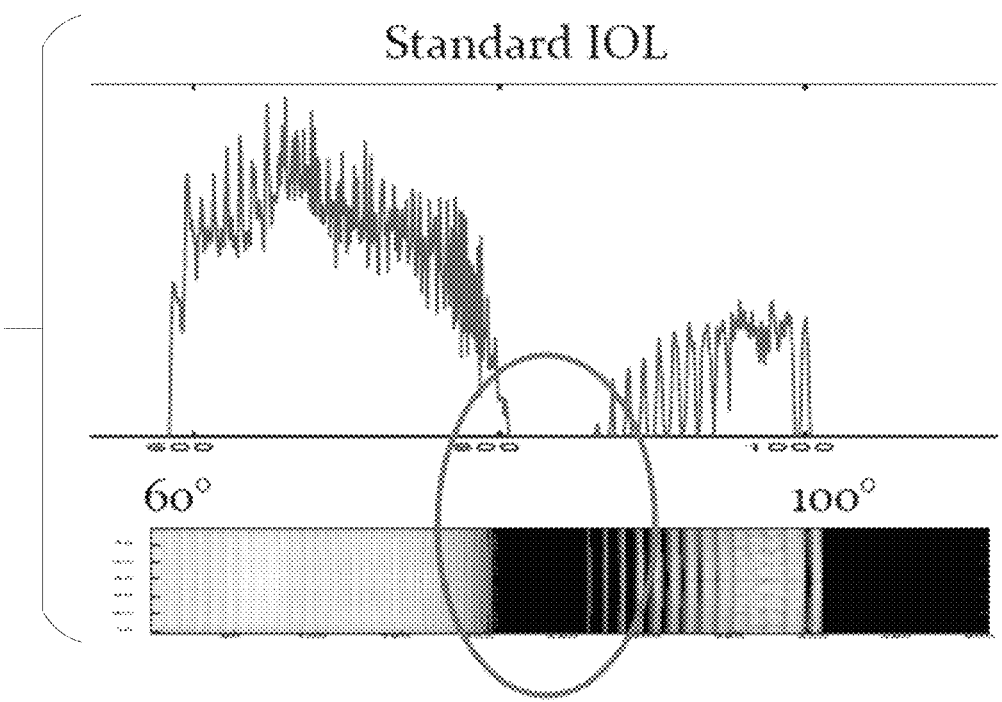
FIG. 19 shows intensity display plots using a standard intraocular lens. A shadow region results from the use of the standard intraocular lens.
Figure 20:
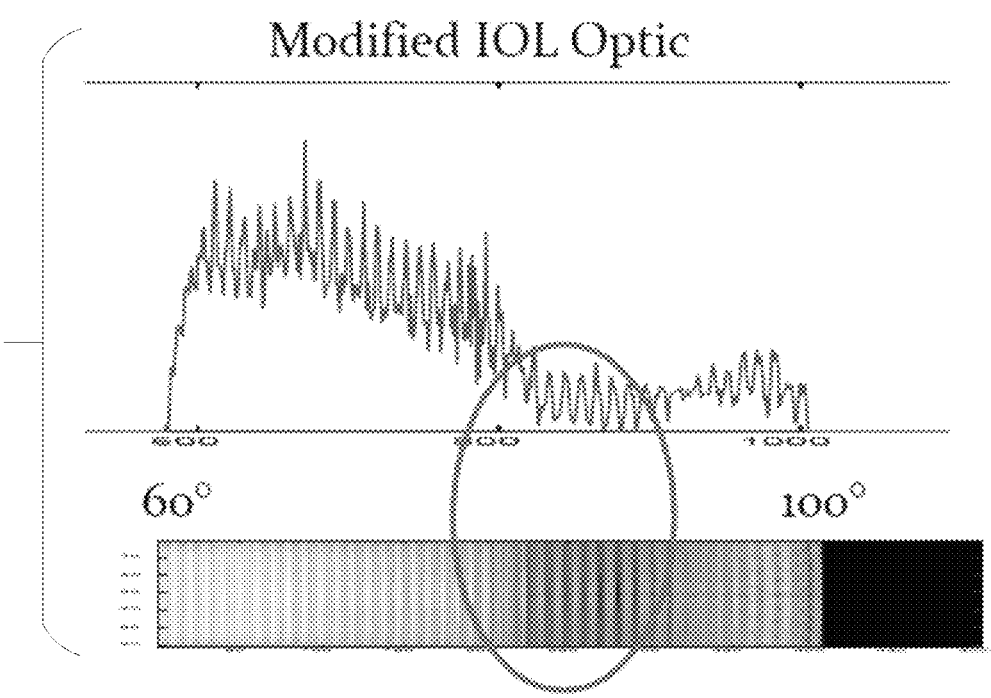
FIG. 20 shows intensity display plots (like FIG. 19) using a modified intraocular lens in accordance with some embodiments described herein. Shadow regions are eliminated.

FIGS. 19 and 20 show a comparison of peripheral retina illumination while using a standard/conventional IOL (FIG. 19) and a "modified" IOL with a concave posterior peripheral portion (FIG. 20) as described herein. FIG. 19 shows a shadowed region, absent illumination. The same area of FIG. 20 has intensities that are greater than zero, indicating illumination and the elimination of shadowed regions. (The sharp oscillations of the intensity are artifacts of the simulation conditions, not actual individual intensity spikes.)

Figure 12:
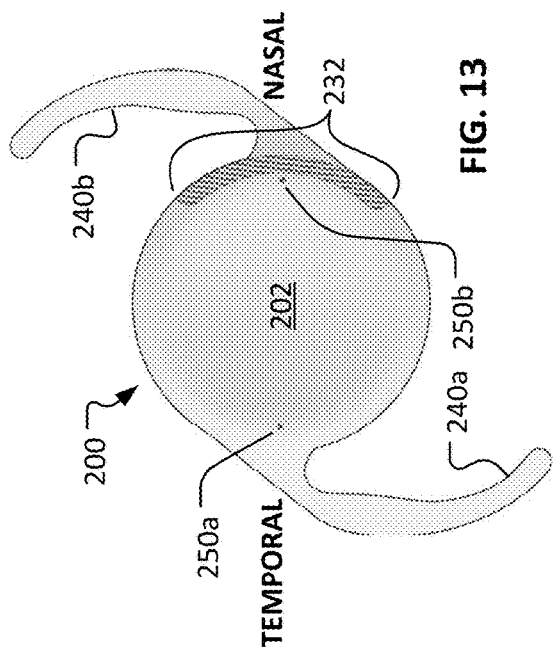
FIG. 12 shows a plan view of the intraocular lens of FIG. 4 with a fiducial marker near the nasal orientation relative to the eye.

FIG. 12 again illustrates intraocular lens 100. In this embodiment, optional fiducial markers 150a and 150b are included. Fiducial markers 150a and 150b can be used by a surgeon during the surgery to visually orient intraocular lens 100 relative to the eye in a desired nasal location or orientation. In this embodiment, posterior peripheral concave peripheral portion 132 is bisected by the nasal position, and by fiducial marker 150b. That is, half of concave peripheral portion 132 is above the nasal position (and fiducial marker 150b) and the other half of concave peripheral portion 132 is below the nasal position (and fiducial marker 150b). While in the depicted embodiment, two haptic members 140a and 140b are included, in some embodiments four haptic members (for four-point fixation) are included.

Figure 13:
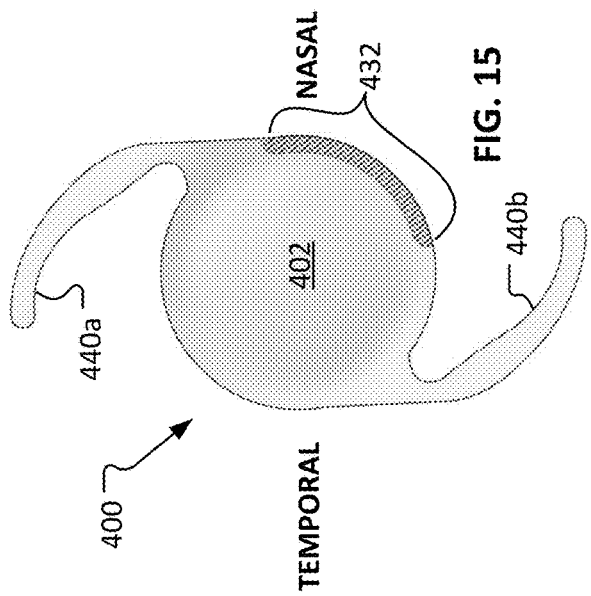
FIG. 13 shows a plan view of another example intraocular lens in accordance with some embodiments described herein.

FIG. 13 illustrates another example intraocular lens 200. In this example, a posterior peripheral concave portion 232 is located at the junction between a lens 202 and a haptic member 240b. In other words, concave portion 232 is located at the haptic-optic junction. In some cases, concave portion 232 is centered with respect to the haptic-optic junction, but such an orientation is not required in all embodiments. In some embodiments, the concave surface profile of concave portion 232 can extend into a portion of haptic member 240b (even beyond what is illustrated in FIG. 13). In some embodiments, the concave surface profile of concave portion 232 abruptly ends at the arcuate junction between the round lens 202 and haptic member 240b (the haptic-optic junction), as depicted. The surface of the portion of haptic member 240b near the haptic-optic junction can be flat or contoured in any manner desired. In some embodiments, the haptic-optic junction can thereby be exploited to maximize uniform illumination of the peripheral retina by refracted light, to provide additional enhanced effects to reduce instances of dysphotopsia after cataract surgery.

Still referring to FIG. 13, the portion of posterior surface modification is in proximity to a haptic member 240b and/or 240a on the nasal side and/or temporal side. In one example, a lens (e.g., 1.55 index material) was modeled with a cone of haptic material outside the 6 mm diameter optic (of 0.21 mm optic edge thickness) that goes to 7.5 mm diameter (of 0.43 mm haptic thickness) representing the optic-haptic junction, and is then flat (at 0.43 mm haptic thickness) out to the haptic tip.

Figure 21:
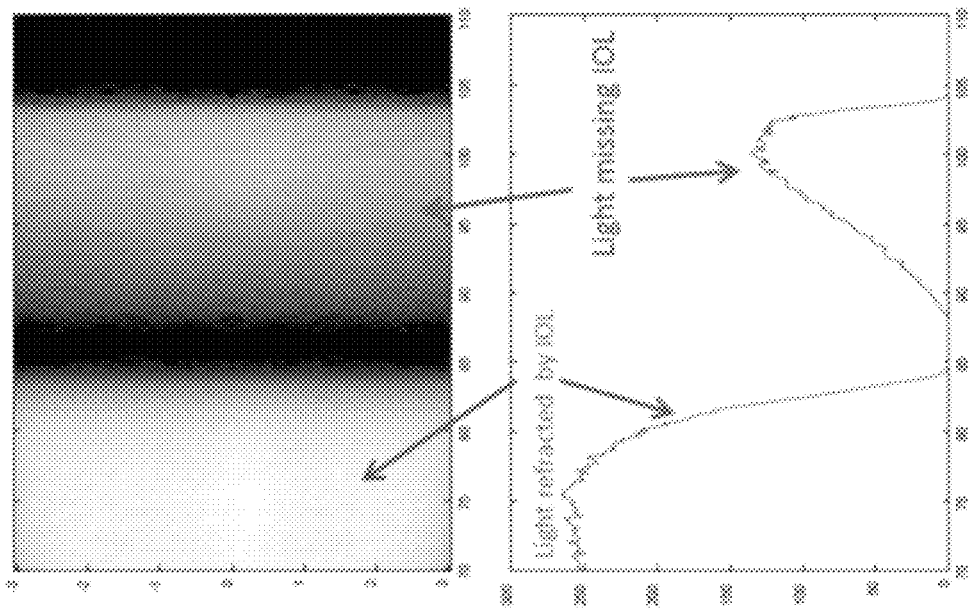
FIG. 21 shows another example light intensity display plot for a standard biconvex IOL. In this example, some light received on the peripheral retina has bypassed the intraocular lens, resulting in the undesirable black band bounded and framed by the two light bands. The band on the left is from light refracted by the optic as intended, and the band on the right is from light that missed the optic.

Referring to FIG. 21, if the standard biconvex intraocular lens like FIG. 19 is used, another light intensity display plot illustrates that in some cases light can bypass the 6.0 mm optic at IOL edge and create the illuminated area (labeled "Light missing IOL") representing ND, that is the dark band (absent light) between this bypassing light and the main white band on the left of the plot of FIG. 21.

Figure 22:
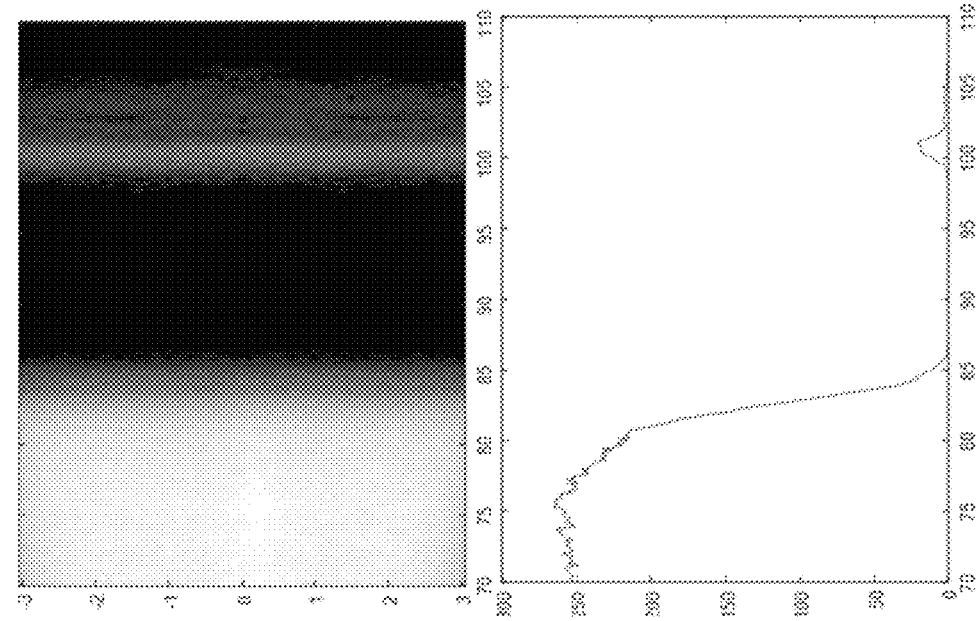
FIG. 22 shows a light intensity display plot using an example standard intraocular lens at the optic-haptic junction. This plot shows how the optic-haptic junction can be used to eliminate the peripheral band of light that bounds the undesirable black band shown in FIG. 21, and to thereby make the dark shadow less noticeable as it is not framed by bands of bright light.

Referring to FIG. 22, if the example intraocular lens 200 of FIG. 13 is used, the light that bypassed the IOL edge of the 6.0 mm optic (as depicted in FIG. 21) instead hits the extended surface(s) of the optic-haptic junction and is refracted into a different direction, or is internally reflected, eliminating most of the second band of light (that was labeled "Light missing IOL" in FIG. 21) that creates the ND.

Figure 23:
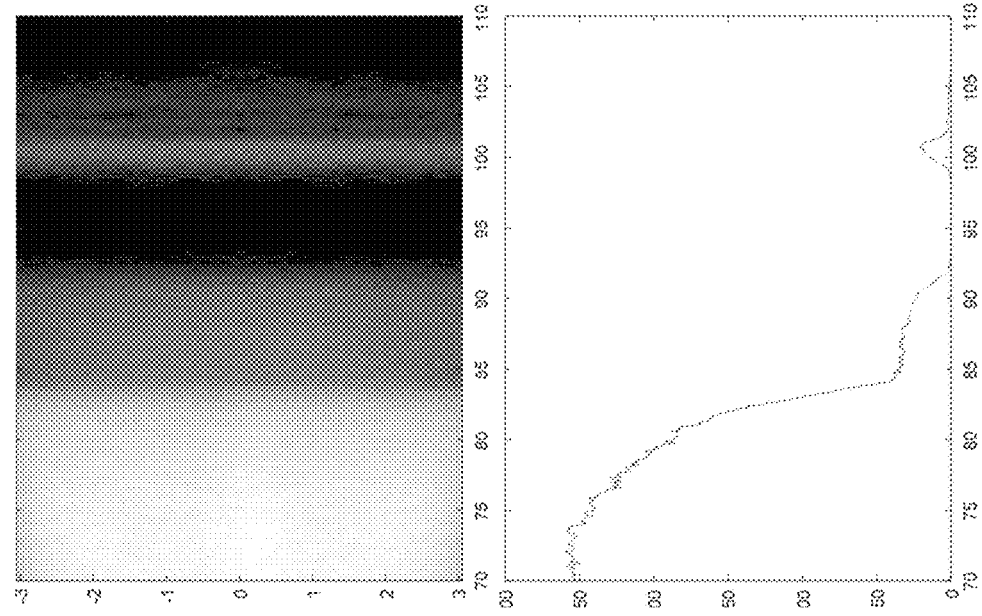
FIG. 23 shows a light intensity display plot of another example intraocular lens at the optic-haptic junction with a posterior surface that includes a modified localized concave peripheral portion of optic located at the optic-haptic junction.
Figure 24:
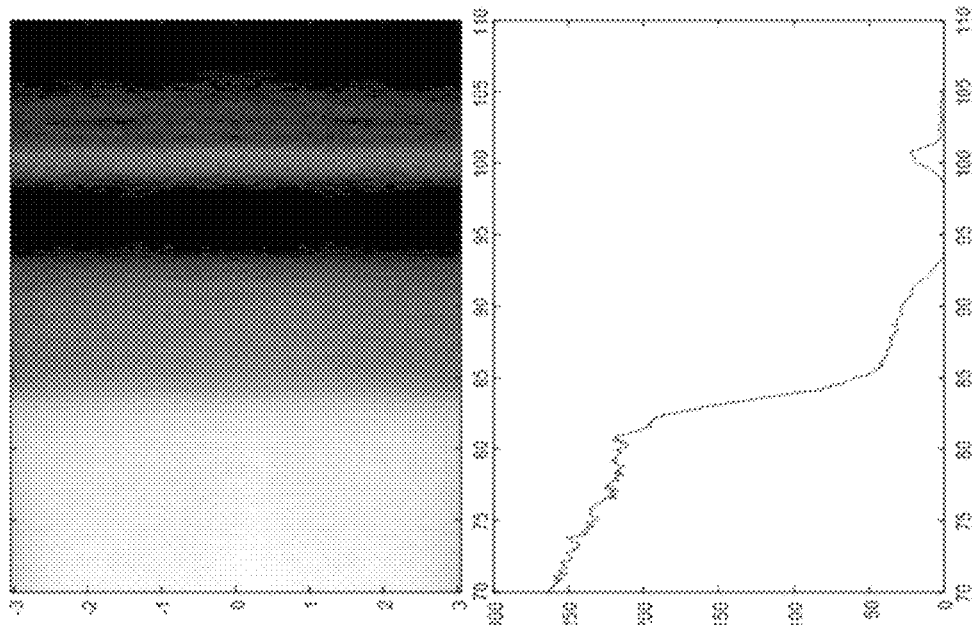
FIG. 24 shows a light intensity display plot of another example intraocular lens at the optic-haptic junction with a posterior surface that includes a modified localized concave peripheral portion of optic located at and extending into the haptic junction located at the optic-haptic junction.

In selected configurations, there is an additive effect to reduce ND further when the posterior surface modification described in this disclosure is located at an optic-haptic junction oriented to the horizontal meridian. FIGS. 23 and 24 illustrate this reduction of the dark band extent, in two light intensity display plots of additional intraocular lens configurations that have a posterior concave peripheral portion located at or along the junction between the lens and a haptic-optic junction (e.g., as depicted in FIG. 13). In each of these cases, the concave annulus has a radius of curvature of 30 mm and is 0.5 mm wide, but is surrounding a central posterior optic of a different diameter. In FIG. 23, the modification extends only to the 6.0 mm optic diameter, but in FIG. 24 the modification extends slightly into the optic-haptic junction itself at a diameter of 6.5 mm (but not the full 7.5 mm described in reference to FIG. 13). Based on these plots, and the bands from about 85 to 93 degrees which are gray instead of the previous black, it can be envisioned that ND can be mitigated or prevented using such an intraocular lens design. Some light that might otherwise bypass the IOL edge beneficially passes through the haptic or optic-haptic junction, and other light is redirected by the modified concave posterior periphery.

Figure 14:
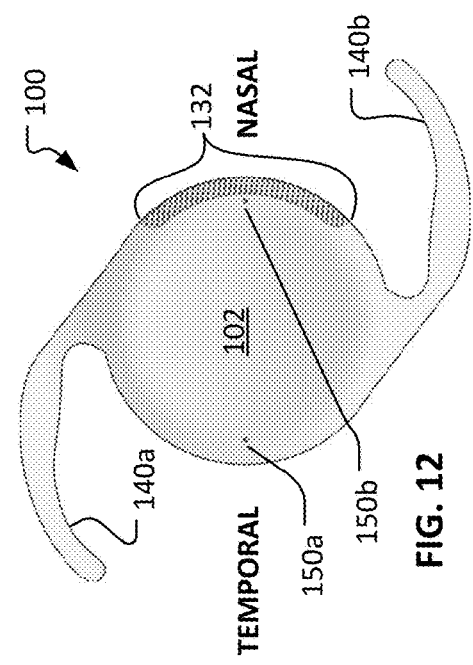
FIG. 14 shows a plan view of another example intraocular lens in accordance with some embodiments described herein.

FIG. 14 illustrates another example intraocular lens 300. In this example, a posterior peripheral concave portion 332 is biased at a slightly inferior position. In other words, a greater percentage of the length of concave portion 332 is inferior of the nasal position as compared to superior to the nasal position.

Figure 15:
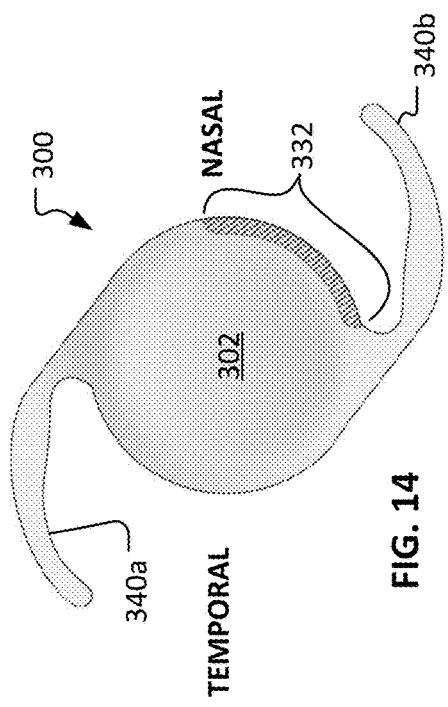
FIG. 15 shows a plan view of another example intraocular lens in accordance with some embodiments described herein.

FIG. 15 illustrates another example intraocular lens 400. This example also has a posterior peripheral concave portion 432 that is biased to a slightly inferior position. Here this is based on the surgical placement of the haptic members 440a and 440b extending superiorly and inferiorly from the edge of intraocular lens 400.

As illustrated by FIGS. 12-15, all the embodiments described herein can have their haptic members (e.g., haptic members 140a-b, 240a-b, 340a-b, and 440a-b) and their peripheral concave portions (e.g., peripheral concave portions 132, 232, 332, and 432) oriented in any desired location relative to the nasal and temporal positions. Any and all combinations and permutations of such features, and all other features described herein, are within the scope of this disclosure.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A method of treating an eye, the method comprising:
implanting an intraocular lens (IOL) in the eye, the intraocular lens comprising an optic comprising:

an anterior surface bounded by a peripheral edge, wherein the peripheral edge is substantially cylindrical; and a posterior surface bounded by the peripheral edge and opposing the anterior surface, wherein the posterior surface includes a concave portion; and two or more haptic members extending from the peripheral edge at respective haptic-optic junctions, wherein all other portions of the posterior surface other than the concave portion are convex, and wherein an entirety of the anterior surface is convex, wherein the concave portion extends along a portion of the posterior surface adjacent to a junction of the posterior surface and the peripheral edge, wherein the peripheral edge extends 360 degrees and the concave peripheral portion extends along the portion of the posterior surface from between 80 degrees to 140 degrees, wherein the intersection of the concave portion and the peripheral edge defines a sharp edge, wherein, when the intraocular lens is finally implanted in a patient's eye, the concave portion is positioned at an approximately nasal orientation relative to the eye, wherein the intraocular lens is designed to reduce positive and negative dysphotopsias after cataract surgery.

2. The method of claim 1, wherein the intraocular lens further comprises at least one fiducial marker located on the intraocular lens, and wherein the method further comprises aligning the at least one fiducial marker near the nasal orientation relative to the eye.

\* \* \* \* \*